United States Patent
Craig

(10) Patent No.: US 7,445,749 B2
(45) Date of Patent: *Nov. 4, 2008

(54) STAINLESS STEEL ALLOY HAVING LOWERED NICKEL CHROMIUM TOXICITY AND IMPROVED BIOCOMPATIBILITY

(75) Inventor: Charles Horace Craig, Lakeside, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/352,458

(22) Filed: Jan. 28, 2003

(65) Prior Publication Data

US 2003/0194343 A1 Oct. 16, 2003

Related U.S. Application Data

(63) Continuation of application No. 09/854,000, filed on May 11, 2001, now Pat. No. 6,582,652.

(51) Int. Cl.
 *C22C 38/18* (2006.01)
(52) U.S. Cl. ........................................... 420/35
(58) Field of Classification Search .............. 420/584.1, 420/583, 43, 34, 35; 148/325, 327, 335–333; 606/198
 See application file for complete search history.

(56) References Cited

U.S. PATENT DOCUMENTS

| | | | |
|---|---|---|---|
| 3,876,475 A | 4/1975 | Ramqvist | |
| 4,155,752 A * | 5/1979 | Oppenheim et al. | 420/40 |
| 4,305,755 A * | 12/1981 | Wilde | 420/82 |
| 4,371,394 A | 2/1983 | Henthorne et al. | |
| 4,761,187 A * | 8/1988 | Paton et al. | 148/542 |
| 4,775,426 A | 10/1988 | Murley et al. | |
| 5,000,912 A | 3/1991 | Bendel et al. | |
| 5,019,337 A * | 5/1991 | Waterstrat | 420/580 |
| 5,147,602 A * | 9/1992 | Andresen et al. | 420/35 |
| 5,151,248 A * | 9/1992 | Ebara et al. | 420/35 |
| 5,169,597 A | 12/1992 | Davidson et al. | |
| 5,395,583 A * | 3/1995 | Potgieter et al. | 420/67 |
| 5,415,704 A | 5/1995 | Davidson | |
| 5,449,373 A * | 9/1995 | Pinchasik et al. | 606/198 |
| 5,477,864 A | 12/1995 | Davidson | |
| 5,498,302 A | 3/1996 | Davidson | |
| 5,501,834 A * | 3/1996 | Nakasuji et al. | 420/36 |
| 5,509,933 A | 4/1996 | Davidson et al. | |
| 5,545,227 A | 8/1996 | Davidson et al. | |
| 5,562,730 A | 10/1996 | Davidson | |
| 5,583,900 A * | 12/1996 | Kasahara et al. | 376/288 |
| 5,636,641 A * | 6/1997 | Fariabi | 600/585 |
| 5,683,442 A | 11/1997 | Davidson | |
| 5,685,306 A | 11/1997 | Davidson | |
| 5,690,670 A | 11/1997 | Davidson | |
| 5,713,947 A | 2/1998 | Davidson | |
| 5,714,115 A * | 2/1998 | Speidel et al. | 420/65 |
| 5,716,400 A | 2/1998 | Davidson | |
| 5,782,910 A | 7/1998 | Davidson | |
| 5,788,368 A * | 8/1998 | Anderson et al. | 366/129 |
| 5,853,419 A * | 12/1998 | Imran | 623/1.15 |
| 5,906,791 A * | 5/1999 | Angeliu | 420/40 |
| 6,267,921 B1 * | 7/2001 | Montagnon et al. | 420/57 |
| 6,325,824 B2 * | 12/2001 | Limon | 623/1.2 |
| 6,391,253 B1 * | 5/2002 | Tochihara et al. | 420/35 |
| 6,419,693 B1 * | 7/2002 | Fariabi | 623/1.18 |
| 6,582,652 B2 * | 6/2003 | Craig | 420/35 |
| 6,666,930 B2 * | 12/2003 | Aoyama et al. | 148/306 |
| 6,767,418 B1 * | 7/2004 | Zhang et al. | 148/421 |

FOREIGN PATENT DOCUMENTS

| | | | |
|---|---|---|---|
| JP | 355131157 A | | 10/1980 |
| WO | WO99/47721 | * | 9/1999 |
| WO | 01/41829 | | 6/2001 |
| WO | WO02/078764 | * | 10/2002 |

OTHER PUBLICATIONS

Gebeau,R.C. et al., "Biomedical Implant Alloy", Advanced Materials & Procedures, Sep. 2001, vol. 159, No. 9, pp. 46-48.*
English Translation of JP 55-131157, Oct. 11, 1980.*
Köster, Ralf et al., Nickel and Molybdenum Contact Allergies in Patients With Coronary In-Stent Restenosis, Lancet, 2000;356:1895-1897, Hamburg, Germany.

* cited by examiner

*Primary Examiner*—John P. Sheehan
*Assistant Examiner*—Jessee Roe
(74) *Attorney, Agent, or Firm*—Fish & Richardson P.C.

(57) ABSTRACT

The present invention is directed towards an austenitic, stainless steel series 300 alloy having improved biocompatible characteristics. The modified stainless steel alloy consists essentially of, in weight percent, about

| C | Mn | Si | P | S |
|---|---|---|---|---|
| ≤0.030 | ≤2.00 | ≤0.750 | ≤0.023 | ≤0.010 |
| Cr | Mo | Ni | Fe | "X" |
| 8.5-11.5 | 0.0-6.25 | 6.5-7.5 | 46.185-74.000 | 5.0-10.0 | whereby variable "x" could be comprised from a group consisting of Gold, Osmium, Palladium, Platinum, Rhenium, Tantalum, or Tungsten. The alloy provides a unique combination of strength, ductility, corrosion resistance, and other mechanical properties which also has improved biocompatible characteristics.

32 Claims, No Drawings

STAINLESS STEEL ALLOY HAVING LOWERED NICKEL CHROMIUM TOXICITY AND IMPROVED BIOCOMPATIBILITY

CROSS-REFERENCE TO RELATED APPLICATIONS

This application is a continuation (and claims the benefit of priority under 35 U.S.C. §120) of U.S. Ser. No. 09/854,000, filed on May 11, 2001 now U.S. Pat. 6,582,652, hereby incorporated by reference.

BACKGROUND OF THE INVENTION

This invention relates to an implantable austenitic stainless steel alloy, and in particular to such an alloy and articles made therefrom in which the elements comprising the alloy are carefully selected and the thermal treatment cycles are closely controlled to prevent ordered phases and thus provide a unique combination of biofunctionality (e.g., high yield strength, good ductility, and good low-cycle fatigue resistance and resistance to stress corrosion, cracking, and pitting), and highly improved biocompatible characteristics due to lowered nickel-chromium toxicity.

Austenite generally does not exist at room temperature in plain-carbon and low-alloy steels, other than as small amounts of retained austenite that did not transform during rapid cooling. However, in certain high-alloy steels, such as the austenitic stainless steels and Hadfield austenitic manganese steel, austenite is the dominant microstructure. In these steels, sufficient quantities of alloying elements that stabilize austenite at room temperature are present (e.g., manganese and nickel). The crystal structure of austenite is face-centered cubic (fcc) as compared to ferrite, which has a body centered cubic (bcc) lattice. A fcc alloy has certain desirable characteristics; for example, it has low-temperature toughness, excellent weldability, and is nonmagnetic. Because of their high alloy content, austenitic steels are usually corrosion resistant. Disadvantages of the austenitic steels are their relative high costs, their susceptibility to stress-corrosion cracking (certain austenitic steels), the fact that they cannot be strengthened other than by cold working, interstitial solid-solution strengthening.

The austenitic stainless steels (e.g., type 301, 302, 303, 304, 305, 308, 309, 310, 314, 316, 317, 321, 330, 347, 348, and 384) generally contain from 6 to 22% nickel to stabilize the austenite microstructure at room temperature. They also contain other alloying elements, such as chromium (16 to 26%) for corrosion resistance, and smaller amounts of manganese and molybdenum. The widely used type 304 stainless steel contains 18 to 20% Cr and 8 to 10.5% Ni, and is also called 18-8 stainless steel. The yield strength of annealed type 304 stainless steel is typically 290 MPa (40 ksi), with a tensile strength of about 580 MPa (84 ksi). However, both yield and tensile strength can be substantially increased by cold working. However, the increase in strength is offset by a substantial decrease in ductility, for example, from about 55% elongation in the annealed condition to about 25% elongation after cold working.

Some austenitic stainless steels (type 200, 201, 202, and 205) employ interstitial solid-solution strengthening with nitrogen addition. Austenite, like ferrite, can be strengthened by interstitial elements such as carbon and nitrogen. However, carbon is usually excluded because of the deleterious effect associated with precipitation of chromium carbides on austenite grain boundaries (a process called sensitization). These chromium carbides deplete the grain-boundary regions of chromium, and the denuded boundaries are extremely susceptible to corrosion. Such steels can be desensitized by heating to high temperature to dissolve the carbides and place the chromium back into solution in the austenite. Nitrogen, on the other hand, is soluble in austenite and is added for strengthening. To prevent nitrogen from forming deleterious nitrides, manganese is added to lower the activity of nitrogen in the austenite, as well as to stabilize the austenite. For example, type 201 stainless steel has composition ranges of 5.5 to 7.5% Mn, 16 to 18% Cr, 3.5 to 5.5% Ni, and 0.25% N. The other type 2xx series of steels contain from 0.25 to 0.40% N.

Another important austenitic steel is austenitic manganese steel. Developed by Sir Robert Hadfield in the late 1890s, these steels remain austenitic after water quenching and have considerable strength and toughness. A typical Hadfield manganese steel contains 1 to 14% Mn, 0.95 to 1.4% C, and 0.3 to 1% Si. Solution annealing is necessary to suppress the formation of iron carbides. The carbon must be in solid solution to stabilize the austenite. When completely austenitic, these steels can be work hardened to provide higher hardness and wear resistance. A work hardened Hadfield manganese steel has excellent resistance to abrasive wear under heavy loading. Because of this characteristic, these steels are ideal for jaw crushers and other crushing and grinding components in the mining industry. Also, Hadfield manganese steels have long been used for railway frogs (components used at the junction point of two railroad lines).

AISI Types 304L, 316L, 321 and 347 stainless steels are austenitic, chromium-nickel and chromium-nickel-molybdenum stainless steels having the following compositions in weight percent:

|    | Type 304 L wt. % | Type 316 L wt. % | Type 321 wt. % | Type 347 wt. % |
|----|------------------|------------------|----------------|----------------|
| C  | 0.03 max | 0.03 max | 0.08 max | 0.08 max |
| Mn | 2.00 max | 2.00 max | 2.00 max | 2.00 max |
| Si | 1.00 max | 1.00 max | 1.00 max | 1.00 max |
| P  | 0.045 max | 0.045 max | 0.045 max | 0.045 max |
| S  | 0.03 max | 0.03 max | 0.03 max | 0.03 max |
| Cr | 18.0-20.0 | 16.0-18.0 | 17.0-19.0 | 17.0-19.0 |
| Ni | 8.0-12.0 | 10.-14.0 | 9.0-12.0 | 9.0-13.0 |
| N  | 0.10 max | 0.10 max | 0.10 max | — |
| Mo | — | 2.0-3.0 | — | — |
| Fe | Bal. | Bal. | Bal. | Bal. |

Source: METALS HANDBOOK RTM. Desk Edition; Chapt. 15, pages 2-3; (1985). The AMS standards for these alloys restrict copper to not more than 0.75%.

The above-listed chromium-nickel and chromium-nickel-molybdenum stainless steels are known to be useful for applications which require good non-magnetic behavior, in combination with good corrosion resistance. One disadvantage of the series 300 stainless steels is their potentially poor biocompatibility, due principally to nickel-chromium toxicity. Therefore, this present invention alloy can be useful in clinical indications because it can provide improved biocompatibility due to lowered nickel-chromium percentages and therefore less toxicity.

Given the foregoing, it would be highly desirable to have an austenitic stainless steel that provides better biocompatibility than is provided by the known austenitic stainless steels.

SUMMARY OF THE INVENTION

The invention generally relates to an implantable austenitic stainless steel alloy that provides better biocompatibility than is provided by the known austenitic stainless steels. One application for the present invention is to use the austenitic stainless steel alloy with increased biocompatibility for fabricating intravascular stents. Typically stents are fabricated from a variety of stainless steels, with the 316 series representing a large percentage of the stainless steel used to fabricate currently marketed stents. The typical composition of 316 series implant grade stainless steel is shown in Table I.

TABLE I

| | Component (%) | | | | | | | |
|---|---|---|---|---|---|---|---|---|
| | C | Mn | Si | P | S | Cr | Mo | Ni | Fe |
| Standard 316 | ≦0.030 | ≦2.000 | ≦1.000 | ≦0.025 | ≦0.010 | 17.000-19.000 | 2.25-3.50 | 13.000-15.000 | Balance |

While the 300 series of stainless steel has several characteristics, such as strength, flexibility, fatigue resistance, biocompatibility, etc. rendering it a good material to make an intravascular stent, one significant disadvantage of 316 series stainless steel, as well as other 300 series of stainless steel, is that they have relatively high nickel-chromium percentages and therefore have the potential for toxicity and poor biocompatibility. A need has arisen to modify the stainless steel composition so it has improved biocompatible properties while at the same time, maintaining those characteristics which render it as a material of choice for implants.

Modified stainless steel of the 300 series for increasing biocompatible characteristics could be produced by creating alloys containing varying amounts of elements that have dense mass and biocompatible characteristics. The chemical make-up of standard series 300 stainless steel, using series 316 as an example, along with the possible chemical ranges of various such alloys are shown on the following Table II. One example of this alloy employs molybdenum in the composition while another example does not use the molybdenum element.

An other object of the present invention is to provide a material which has superior properties, including biocompatibility, for fabricating any intravascular implants or stents.

DETAILED DESCRIPTION

The alloy according to the present invention comprises a stainless steel series 300 compound used to fabricate a stent which replaces a portion of the iron or molybdenum component of the 300 series with one or combination of several elements containing relatively non-toxic properties. Examples of such elements are gold (Au), osmium (Os), palladium (Pd), platinum (Pt), rhenium (Re), tantalum (Ta) or tungsten (W). The alloy has reduced toxicity potential containing a range of 2.0 to 10.0 percent of one or more of these elements, with a preferred range of 4.0 to 5.0 percent. It is anticipated that various combinations of the biocompatible elements can be used to replace the iron or molybdenum component without adversely affecting the ability to form austenite.

The foregoing, as well as additional objects and advantages of the present invention, achieved in a series 300 stainless steel alloy, is compared with standard 316 stainless steel and summarized in Tables III through X below, containing in weight percent, about:

TABLE II

| | Component (%) | | | | | | | | |
|---|---|---|---|---|---|---|---|---|---|
| | C | Mn | Si | P | S | Cr | Mo | Ni | X | Fe |
| Standard 316 | 0.020 | 1.760 | 0.470 | 0.014 | 0.002 | 17.490 | 2.790 | 14.680 | 0.000 | 62.774 |
| Modified Alloy With Molybdenum | ≦0.030 | ≦2.000 | ≦1.000 | ≦0.025 | ≦0.010 | 8.50-11.50 | 3.250-6.250 | 6.50-7.50 | 5.000-10.00 | Bal. |
| Modified Alloy without Molybdenum | ≦0.030 | ≦2.000 | ≦1.000 | ≦0.025 | ≦0.010 | 8.50-11.50 | 0.0 | 6.50-7.50 | 5.000-10.00 | Bal. |

Variable "X" could be comprised of or a combination of Au, Os, Pd, Pt, Re, Ta or W.

Other features and advantages of the present invention will become more apparent from the following detailed description of the invention.

It is an object of the present invention to provide an austenitic 300 series stainless steel alloy that provides better biocompatibility than is provided by the known austenitic stainless steels.

TABLE III

| | Component (%) | | | | | | | | |
|---|---|---|---|---|---|---|---|---|---|
| | C | Mn | Si | P | S | Cr | Mo | Ni | Fe | x |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

Where variable "X" could be comprised of or a combination of Au, Os, Pd, Pt, Re, Ta or W.

TABLE IV

| | Component (%) | | | | | | | | |
|---|---|---|---|---|---|---|---|---|---|
| | C | Mn | Si | P | S | Cr | Mo | Ni | Fe | Au |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE V

| | Component (%) | | | | | | | | |
|---|---|---|---|---|---|---|---|---|---|
| | C | Mn | Si | P | S | Cr | Mo | Ni | Fe | Os |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE VI

| | Component (%) | | | | | | | | |
|---|---|---|---|---|---|---|---|---|---|
| | C | Mn | Si | P | S | Cr | Mo | Ni | Fe | Pd |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE VII

| | Component (%) | | | | | | | | |
|---|---|---|---|---|---|---|---|---|---|
| | C | Mn | Si | P | S | Cr | Mo | Ni | Fe | Pt |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE VIII

| | Component (%) | | | | | | | | |
|---|---|---|---|---|---|---|---|---|---|
| | C | Mn | Si | P | S | Cr | Mo | Ni | Fe | Re |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE IX

| | Component (%) | | | | | | | | |
|---|---|---|---|---|---|---|---|---|---|
| | C | Mn | Si | P | S | Cr | Mo | Ni | Fe | Ta |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

TABLE X

| | Component (%) | | | | | | | | | |
|---|---|---|---|---|---|---|---|---|---|---|
| | C | Mn | Si | P | S | Cr | Mo | Ni | Fe | W |
| Standard 316 | 0.020 | 1.760 | 0.470 | 0.014 | 0.002 | 17.490 | 2.790 | 14.680 | 62.774 | 0.00 |
| Modified Alloy | ≦0.030 | ≦2.000 | ≦0.750 | ≦0.023 | ≦0.010 | 8.5-11.5 | 0.0-6.25 | 6.5-7.5 | 46.185-74.000 | 5.0-10.0 |

The alloy for fabricating a series 300 stainless steel with improved biocompatible properties can contain up to 0.03% of carbon. The carbon element contributes to good hardness capability and high tensile strength by combining with other elements such as chromium and molybdenum to form carbides during beat treatment. However, too much carbon adversely affects the fracture toughness of this alloy.

Chromium contributes to the good hardenability corrosion resistance and hardness capability of this alloy and benefits the desired low ductile-brittle transition temperature of the alloy. However, due to its potential for toxicity, the percentage of chromium is maintained within the range of 8.5 to 11.5 percent.

Nickel contributes to the hardenability of this alloy such that the alloy can be hardened with or without rapid quenching techniques. Nickel benefits the fracture toughness and stress corrosion cracking resistance provided by this alloy and contributes to the desired low ductile-to-brittle transition temperature. However, due to its potential for toxicity, the percentage of Nickel is maintained within the range of 13-15 percent.

Molybdenum is present in this alloy because it benefits the desired low ductile brittle transition temperature of the alloy. Above about 3% molybdenum, the fracture toughness of the alloy is adversely affected. Preferably, molybdenum is limited to not more than about 1.2%. However, the entire portion of the molybdenum can be replaced with certain biocompatible elements such as Pt without adversely affecting the desired characteristics of the alloy.

The alloy for fabricating a series 300 stainless steel with biocompatible properties can also contain up to 2.0% manganese. Manganese is partly depended upon to maintain the austenitic, nonmagnetic character of the alloy. Manganese also plays a role, in part, providing resistance to corrosive attack.

The balance of the alloy according to the present invention is essentially iron except for the usual impurities found in commercial grades of alloys intended for similar service or use. The levels of such elements must be controlled so as not to adversely affect the desired properties of this alloy. For example, phosphorus is limited to not more than about 0.008% and sulfur is limited to not more 0.004%. In addition, the alloy for fabricating a series 300 stainless steel alloy with biocompatible properties can contain up to 0.75% silicon. Furthermore, the alloy for fabricating a series 300 stainless steel stent with biocompatible properties can contain up to 0.023% and 0.002% phosphorus and sulfur, respectively, without affecting the desirable properties.

No special techniques are required in melting, casting, or working the alloy of the present invention. The alloy of the present invention is readily melted using conventional and/or vacuum melting techniques. For best results, as when additional refining is desired, a multiple melting practice is preferred. The preferred practice is to heat a melt in a vacuum induction furnace (VIM) and cast the melt in the form of an electrode. The electrode is then remelted in a vacuum arc furnace (VAR) and recast into one or more ingots.

The alloy of the present invention can be formed into a variety of shapes for a wide variety of uses and lends itself to the formation of billets, bars, rod, wire, strip, plate, or sheet using conventional practices. As an example, the alloy can be prepared from melts which can be heated under argon cover and cast as ingots. The ingots can be maintained at a temperature range of 2100-2300° F. (1149-1260°C.) for 2 hours and then pressed into billets. The billets may be ground to remove surface defects and the ends cut off. The billets can then be hot rolled to form intermediate bars with an intermediate diameter. The intermediate bars are hot rolled to a diameter of 0.7187 in. (1.82 cm) from a temperature range of 2100-2300° F. (1149-1260° C.). The round bars are straightened and then turned to a final diameter. All of the bars can be pointed, solution annealed, water quenched, and acid cleaned to remove surface scale.

The alloy according to the present invention can be useful in a variety of applications requiring high strength and biocompatible characteristics, for example, to fabricate stents of other medical applications.

It is apparent from the foregoing description and the accompanying examples, that the alloy according to the present invention provides a unique combination of tensile strength and biocompatible characteristics not provided by known series 300 stainless steel alloys. This alloy is well suited to applications where high strength and biocompatibility are required.

The terms and expressions which have been employed herein are used as terms of description and not of limitation. There is no intention in the use of such terms and expressions to exclude any equivalents of the features described or any portions thereof It is recognized, however, that various modifications are possible within the scope of the invention claimed.

While the invention has been illustrated and described herein in terms of its use as an intravascular stent, it will be apparent to those skilled in the art that the stent can be used in other instances such as to expand prostate urethras in cases of prostate hyperplasia. Other modifications and improvements may be made without departing from the scope of the invention.

The terms and expressions that have been employed herein are used as terms of description and not of limitation. There is no intention in the use of such terms and expressions to exclude any equivalents of the features described or any portions thereof. It is recognized, however, that various modifications are possible within the scope of the invention claimed. Other modifications and improvements can be made to the invention without departing from the scope thereof.

I claim:

1. A stent, comprising:
   a member capable of supporting a body passageway, the member being formed of a non-magnetic, austenitic steel alloy comprising between about 8.5 and 11.5 weight percent of chromium,
between about 2.0 and about 10 weight percent of a first element selected from the group consisting of gold, osmium, palladium, platinum, and rhenium, and iron.

2. The stent of claim 1, wherein the alloy further comprises less than 7.5 weight percent of nickel.

3. The stent of claim 1, wherein the alloy further comprises between about 6.5 and 7.5 weight percent of nickel.

4. The stent of claim 1, wherein the first element is platinum.

5. The stent of claim 1, wherein the alloy comprises between about 5 and about 10 weight percent of the first element.

6. The stent of claim 1, wherein the alloy comprises a combination of first elements.

7. The stent of claim 1, wherein the alloy further comprises molybdenum.

8. The stent of claim 7, wherein the alloy comprises less than about 6.25 weight percent of molybdenum.

9. The stent of claim 1, wherein the alloy further comprises manganese.

10. The stent of claim 9, wherein the alloy comprises less than about 2 weight percent of manganese.

11. A stent, comprising:
a member capable of supporting a body passageway, the member being formed of a non-magnetic, austenitic alloy comprising iron, chromium, a first element selected from the group consisting of gold, osmium, palladium, platinum, and rhenium, and between about 6.5 and 7.5 weight percent nickel, the total amount of chromium and nickel being present at less than about 19 weight percent.

12. The stent of claim 11, wherein the total amount of chromium and nickel is less about 18 weight percent.

13. The stent of claim 11, wherein the total amount of chromium and nickel is less than about 16 weight percent.

14. The stent of claim 11, wherein the alloy comprises more than about 8.5 weight percent of chromium.

15. The stent of claim 11, wherein the alloy comprises between about 8.5 and about 11.5 weight percent of chromium.

16. The stent of claim 11, wherein the first element is platinum.

17. The stent of claim 11, wherein the alloy comprises less than about 10 weight percent of the first element.

18. The stent of claim 16, wherein the alloy comprises between about 5 and about 10 weight percent of the first elements.

19. The stent of claim 16, wherein the alloy comprises a combination of first elements.

20. The stent of claim 11, wherein the alloy further comprises molybdenum.

21. The stent of claim 20, wherein the alloy comprises less than about 6.25 weight percent of molybdenum.

22. The stent of claim 11, wherein the alloy further comprises manganese.

23. The stent of claim 22, wherein the alloy comprises less than about 2 weight percent of manganese.

24. A stent, comprising:
a member capable of supporting a body passageway, the member being formed of a non-magnetic, austenitic alloy comprising
between about 8.5 and 1.5 weight percent of chromium,
between about 6.5 and 7.5 weight percent of nickel,
a first element selected from the group consisting of gold, osmium, palladium, platinum, and rhenium, and
greater than about 46 weight percent of iron.

25. The stent of claim 24, wherein the first element is platinum.

26. The stent of claim 24, wherein the alloy comprises less than about 10 weight percent of the first element.

27. The stent of claim 24, wherein the alloy comprises between about 5 and about 10 weight percent of the first element.

28. The stent of claim 24, wherein the alloy comprises a combination of first elements.

29. The stent of claim 24, wherein the alloy further comprises molybdenum.

30. The stent of claim 29, wherein the alloy comprises less than about 6.25 weight percent of molybdenum.

31. The stent of claim 24, wherein the alloy further comprises manganese.

32. The stent of claim 31, wherein the alloy comprises less than about 2 weight percent of manganese.

* * * * *

UNITED STATES PATENT AND TRADEMARK OFFICE
CERTIFICATE OF CORRECTION

| | |
|---|---|
| PATENT NO. | : 7,445,749 B2 |
| APPLICATION NO. | : 10/352458 |
| DATED | : November 4, 2008 |
| INVENTOR(S) | : Charles Horace Craig |

It is certified that error appears in the above-identified patent and that said Letters Patent is hereby corrected as shown below:

Column 10, line 22 (Claim 24), please delete "1.5" and insert --11.5-- therefor.

Signed and Sealed this

Sixteenth Day of June, 2009

JOHN DOLL
*Acting Director of the United States Patent and Trademark Office*